(12) United States Patent
Cheon et al.

(10) Patent No.: US 7,220,868 B2
(45) Date of Patent: May 22, 2007

(54) PROCESS FOR THE PREPARATION OF NOVEL DYES FOR USE IN IMAGING MEMBERS

(75) Inventors: Kap-Soo Cheon, Shrewsbury, MA (US); Michael P. Filosa, Medfield, MA (US); John L. Marshall, Lexington, MA (US)

(73) Assignee: Zink Imaging, LLC, Waltham, MA (US)

( * ) Notice: Subject to any disclaimer, the term of this patent is extended or adjusted under 35 U.S.C. 154(b) by 0 days.

(21) Appl. No.: 11/369,805

(22) Filed: Mar. 6, 2006

(65) Prior Publication Data

US 2006/0234143 A1 Oct. 19, 2006

Related U.S. Application Data

(63) Continuation of application No. 10/788,963, filed on Feb. 27, 2004, now Pat. No. 7,008,759.

(60) Provisional application No. 60/451,208, filed on Feb. 28, 2003.

(51) Int. Cl.
*C07D 405/00* (2006.01)

(52) U.S. Cl. ........................ 548/463; 546/116

(58) Field of Classification Search .......... 546/18, 546/115, 116; 549/227; 430/332, 338, 200, 430/964, 211; 503/200, 221; 548/463
See application file for complete search history.

(56) References Cited

U.S. PATENT DOCUMENTS

| | | | | |
|---|---|---|---|---|
| 3,929,831 A | * | 12/1975 | Garner et al. | ............... 548/407 |
| 4,390,616 A | * | 6/1983 | Sato et al. | ................... 430/338 |
| 4,405,788 A | * | 9/1983 | Locatell et al. | ............. 546/165 |
| 4,436,920 A | * | 3/1984 | Sato et al. | ................... 549/227 |
| 4,602,263 A | * | 7/1986 | Borror et al. | ................ 503/201 |
| 4,728,633 A | * | 3/1988 | Satomura et al. | ............ 503/221 |
| 6,054,246 A | * | 4/2000 | Bhatt et al. | .................. 430/151 |
| 6,537,410 B2 | * | 3/2003 | Arnost et al. | ................ 156/235 |
| 7,008,759 B2 | * | 3/2006 | Cheon et al. | ................ 430/332 |

FOREIGN PATENT DOCUMENTS

| | | |
|---|---|---|
| EP | 0 568 344 A1 | 11/1993 |
| EP | 588344 | * 11/1993 |
| GB | 2 311 075 A | 9/1997 |
| GB | 2311075 | * 9/1997 |
| JP | 07304972 | * 11/1995 |

OTHER PUBLICATIONS

U.S. Appl. No. 10/789,648, filed Feb. 27, 2004, Chu et al.
U.S. Appl. No. 10/151,432, filed May 20, 2002, Bhatt et al.

* cited by examiner

*Primary Examiner*—Amelia A. Owens
(74) *Attorney, Agent, or Firm*—Michel Morency; James F. Ewing; Foley & Lardner LLP

(57) ABSTRACT

There are described novel rhodamine dye compounds and imaging members and imaging methods, including thermal imaging members and imaging methods, utilizing the compounds. The dye compounds exhibit a first color when in the crystalline form and a second color, different from the first color, when in the liquid, amorphous form.

7 Claims, No Drawings

PROCESS FOR THE PREPARATION OF NOVEL DYES FOR USE IN IMAGING MEMBERS

REFERENCE TO RELATED APPLICATIONS

This application is a continuation application under 35 U.S.C. §120 from U.S. Ser. No. 10/788,963 filed Feb. 27, 2004 now U.S. Pat. No. 7,008,759, which claims the benefit of provisional application Ser. No. 60/451,208, filed Feb. 28, 2003, the contents of both of which are incorporated herein by reference in their entireties.

This application is related to the following commonly assigned United States patent applications and patents, the disclosures of all of which are hereby incorporated by reference herein in their entirety:

U.S. patent application Ser. No. 10/789,648, filed on even date herewith;

U.S. Pat. No. 6,537,410 B2;

U.S. patent application Ser. No. 10/151,432, filed May 20, 2002, (U.S. Patent Application Publication No. US2003/0125206 A1) now U.S. Pat. No. 6,801,233 B2; and U.S. Pat. No. 6,054,246.

FIELD OF THE INVENTION

This invention relates to novel compounds and, more particularly, to compounds which exhibit one color in the crystalline form and a second, different color in the liquid, or amorphous, form. Also described are imaging members and methods, including thermal imaging members and methods, utilizing the compounds.

BACKGROUND OF THE INVENTION

The development of thermal print heads (linear arrays of individually-addressable resistors) has led to the development of a wide variety of thermally-sensitive media. In some of these, known as "thermal transfer" systems, heat is used to move colored material from a donor sheet to a receiver sheet. Alternatively, heat may be used to convert a colorless coating on a single sheet into a colored image, in a process known as "direct thermal" imaging. Direct thermal imaging has the advantage over thermal transfer of the simplicity of a single sheet. On the other hand, unless a fixing step is incorporated, direct thermal systems are still sensitive to heat after thermal printing. If a stable image is needed from an unfixed direct thermal system, the temperature for coloration must be higher than any temperature that the image is likely to encounter during normal use. A problem arises in that the higher the temperature for coloration, the less sensitive the medium will be when printed with the thermal print head. High sensitivity is important for maximum speed of printing, for maximizing the longevity of the print head, and for energy conservation in mobile, battery-powered printers. As described in more detail below, maximizing sensitivity while maintaining stability is more easily achieved if the temperature of coloration of a direct thermal medium is substantially independent of the heating time.

Thermal print heads address one line of the image at a time. For reasonable printing times, each line of the image is heated for about ten milliseconds or less. Storage of the medium (prior to printing or in the form of the final image) may need to be for years, however. Thus, for high imaging sensitivity, a high degree of coloration is required in a short time of heating, while for good stability a low degree of coloration is required for a long time of heating.

Most chemical reactions speed up with increasing temperature. Therefore, the temperature required for coloration in the short heating time available from a thermal print head will normally be higher than the temperature needed to cause coloration during the long storage time. Actually reversing this order of temperatures would be a very difficult task, but maintaining a substantially time-independent temperature of coloration, such that both long-time and short-time temperatures for coloration are substantially the same, is a desirable goal that is achieved by the present invention.

There are other reasons why a time-independent coloration temperature may be desirable. It may, for example, be required to perform a second thermal step, requiring a relatively long time of heating, after printing. An example of such a step would be thermal lamination of an image. The temperature of coloration of the medium during the time required for thermal lamination must be higher than the lamination temperature (otherwise the medium would become colorized during lamination). It would be preferred that the imaging temperature be higher than the lamination temperature by as small a margin as possible, as would be the case for time-independent temperature of coloration.

Finally, the imaging system may comprise more than one color-forming layer and be designed to be printed with a single thermal print-head, as described in the above-mentioned patent application Ser. No. 10/151,432. In one embodiment of the imaging system, the topmost color-forming layer forms color in a relatively short time at a relatively high temperature, while the lower layer or layers form color in a relatively long time at a relatively low temperature. An ideal topmost layer for this type of direct thermal imaging system would have time-independent temperature of coloration.

Prior art direct thermal imaging systems have used several different chemical mechanisms to produce a change in color. Some have employed compounds that are intrinsically unstable, and which decompose to form a visible color when heated. Such color changes may involve a unimolecular chemical reaction. This reaction may cause color to be formed from a colorless precursor, the color of a colored material to change, or a colored material to bleach. The rate of the reaction is accelerated by heat. For example, U.S. Pat. No. 3,488,705 discloses thermally unstable organic acid salts of triarylmethane dyes that are decomposed and bleached upon heating. U.S. Pat. No. 3,745,009 reissued as U.S. Reissue Pat. No. 29,168 and U.S. Pat. No. 3,832,212 disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds that undergo coloration or bleaching, reversibly or irreversibly, via ring-opening and ring-closing in response to activating energies. U.S. Pat. No. 4,720,449 describes an intramolecular acylation reaction that converts a colorless molecule to a colored form. U.S. Pat. No. 4,243,052 describes pyrolysis of a mixed carbonate of a quinophthalone precursor that may be used to form a dye. U.S. Pat. No. 4,602,263 describes a thermally-removable protecting group that may be used to reveal a dye or to change the color of a dye. U.S. Pat. No. 5,350,870 describes an intramolecular acylation reaction that may be used to induce a color change. A further example of a unimolecular color-forming reaction is described in "New Thermo-Response Dyes: Coloration by the Claisen Rearrangement and Intramolecular Acid-Base Reaction Masahiko Inouye, Kikuo Tsuchiya, and Teijiro Kitao, Angew. Chem. Int. Ed. Engl. 31, pp. 204–5 (1992).

In all of the above-mentioned examples, control of the chemical reaction is achieved through the change in rate that occurs with changing temperature. Thermally-induced changes in rates of chemical reactions in the absence of phase changes may often be approximated by the Arrhenius equation, in which the rate constant increases exponentially as the reciprocal of absolute temperature decreases (i.e., as temperature increases). The slope of the straight line relating the logarithm of the rate constant to the reciprocal of the absolute temperature is proportional to the so-called "activation energy". The prior art compounds described above are coated in an amorphous state prior to imaging, and thus no change in phase is expected or described as occurring between room temperature and the imaging temperature. Thus, as employed in the prior art, these compounds exhibit strongly time-dependent coloration temperatures. Some of these prior art compounds are described as having been isolated in crystalline form. Nevertheless, in no case is there mentioned in this prior art any change in activation energy of the color-forming reaction that may occur when crystals of the compounds are melted.

Other prior art thermal imaging media depend upon melting to trigger image formation. Typically, two or more chemical compounds that react together to produce a color change are coated onto a substrate in such a way that they are segregated from one another, for example, as dispersions of small crystals. Melting, either of the compounds themselves or of an additional fusible vehicle, brings them into contact with one another and causes a visible image to be formed. For example, a colorless dye precursor may form color upon heat-induced contact with a reagent. This reagent may be a Bronsted acid, as described in "Imaging Processes and Materials", Neblette's Eighth Edition, J. Sturge, V. Walworth, A. Shepp, Eds., Van Nostrand Reinhold, 1989, pp. 274–275, or a Lewis acid, as described for example in U.S. Pat. No. 4,636,819. Suitable dye precursors for use with acidic reagents are described, for example, in U.S. Pat. No. 2,417,897, South African Patent 68-00170, South African Patent 68-00323 and Ger. Offenlegungsschrift 2,259,409. Further examples of such dyes may be found in "Synthesis and Properties of Phthalide-type Color Formers", by Ina Fletcher and Rudolf Zink, in "Chemistry and Applications of Leuco Dyes", Muthyala Ed., Plenum Press, New York, 1997. The acidic material may for example be a phenol derivative or an aromatic carboxylic acid derivative. Such thermal imaging materials and various combinations thereof are now well known, and various methods of preparing heat-sensitive recording elements employing these materials also are well known and have been described, for example, in U.S. Pat. Nos. 3,539,375, 4,401,717 and 4,415,633. U.S. Pat. Nos. 4,390,616 and 4,436,920 describe image forming members comprising materials similar to those of the present invention. The materials described therein are fluoran dyes for use in conjunction with a developer, and there is not report of image formation upon melting in the absence of a developer.

Prior art systems in which at least two separate components are mixed following a melting transition suffer from the drawback that the temperature required to form an image in a very short time by a thermal print-head may be substantially higher than the temperature required to colorize the medium during longer periods of heating. This difference is caused by the change in the rate of the diffusion needed to mix the molten components together, which may become limiting when heat is applied for very short periods. The temperature may need to be raised well above the melting points of the individual components to overcome this slow rate of diffusion. Diffusion rates may not be limiting during long periods of heating, however, and the temperature at which coloration takes place in these cases may actually be less than the melting point of either individual component, occurring at the eutectic melting point of the mixture of crystalline materials.

As the state of the art in imaging systems advances and efforts are made to provide new imaging systems that can meet new performance requirements, and to reduce or eliminate some of the undesirable characteristics of the known systems, it would be advantageous to have new compounds which can be used as image-forming materials in imaging systems, including thermal imaging systems.

SUMMARY OF THE INVENTION

It is therefore an object of this invention to provide novel compounds.

Another object of the invention is to provide compounds which exhibit different colors when in the crystalline form and in the liquid form.

Yet another object of the invention is to provide imaging members and methods, including thermal imaging members and methods, which utilize the novel compounds.

The present invention provides novel rhodamine compounds that are useful as image dyes in imaging systems. According to one aspect of the invention there are provided novel dye compounds which exhibit a first color when in the crystalline form and a second color, different from the first color, when in the liquid, amorphous form.

In one embodiment of the invention there are provided novel compounds which are represented by formula I

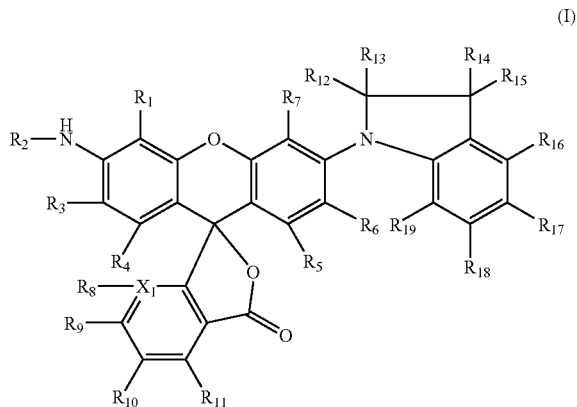

wherein:

$R_1$, $R_3$, $R_4$, $R_5$, $R_6$ and $R_7$ are each independently selected from the group consisting of hydrogen, alkyl, preferably having from 1 to 18 carbon atoms, substituted alkyl, alkenyl, substituted alkenyl, alkynyl, substituted, alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_2$ is selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, sulfonyl, aryl, substituted aryl, heteroaryl, substituted heteroaryl, substituted oxygen, substituted nitrogen and substituted sulfur;

$R_8$ is absent or selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_9$, $R_{10}$ and $R_{11}$ are independently selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_{12}$, $R_{13}$, $R_{14}$ and $R_{15}$ are independently selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, aryl, substituted aryl, heteroaryl, and substituted heteroaryl;

$R_{16}$, $R_{17}$, $R_{18}$ and $R_{19}$ are independently selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur; and $X_1$ is carbon or nitrogen.

In a preferred group of compounds represented by formula I, $R_8$, $R_9$, $R_{10}$ and $R_{11}$ are halogen and $R_1$, $R_2$, $R_3$, $R_4$, $R_5$, $R_6$, $R_7$, $R_{12}$, $R_{13}$, $R_{14}$, $R_{15}$, $R_{16}$, $R_{17}$, $R_{18}$ and $R_{19}$ are as previously defined and $X_1$ is carbon.

The conversion to the liquid form can be carried out by applying heat to the compounds and therefore the compounds are useful in thermal imaging members used in thermal imaging methods. In such thermal imaging methods thermal energy may be applied to the thermal imaging members by any of the techniques known in thermal imaging such as from a thermal print head, a laser, a heated stylus, etc. In another embodiment, the conversion to the liquid form may be effected by applying a solvent for the crystalline solid such as from an ink jet imaging apparatus to at least partially dissolve the crystalline material. In another embodiment, one or more thermal solvents, which are crystalline materials, can be incorporated in the thermal imaging member. The crystalline thermal solvent(s), upon being heated, melt and dissolve or liquefy, and thereby convert, at least partially, the crystalline image-forming material to the liquid amorphous form to form the image.

The compounds of the invention may be incorporated in any suitable thermal imaging members. Typical suitable thermal imaging members generally comprise a substrate carrying at least one image-forming layer including a compound in the crystalline form, which can be converted, at least partially to a liquid in the amorphous form, the liquid having intrinsically a different color from the crystalline form. The thermal imaging member may be monochrome or multicolor and the temperature at which an image is formed in at least one of the image-forming layers is time independent.

Preferred thermal imaging members according to the invention are those having the structures described in prior co-pending commonly assigned U.S. patent application Ser. No. 09/745,700 filed Dec. 20, 2000, now U.S. Pat. No. 6,537,410 B1 which is hereby incorporated herein by reference in its entirety and made a part of this application.

Other preferred thermal imaging members are those having the structures described in prior, co-pending commonly assigned U.S. patent application Ser. No. 10/151,432 filed May 20, 2002 which is hereby incorporated herein by reference in its entirety and made a part of this application.

Further preferred thermal imaging members are those having the structures described in U.S. Pat. No. 6,054,246 which is hereby incorporated herein by reference in its entirety and made a part of this application.

DETAILED DESCRIPTION OF THE INVENTION

Compounds in the crystalline state commonly have properties, including color, that are very different from those of the same compounds in an amorphous form. In a crystal, a molecule is typically held in a single conformation (or, more rarely, in a small number of conformations) by the packing forces of the lattice. Likewise, if a molecule can exist in more than one interconverting isomeric forms, only one of such isomeric forms is commonly present in the crystalline state. In amorphous form or solution, on the other hand, the compound may explore its whole conformational and isomeric space, and only a small proportion of the population of individual molecules of the compound may at any one time exhibit the particular conformation or isomeric form adopted in the crystal. Compounds of the present invention exhibit tautomerism in which at least one tautomeric form is colorless, and at least another tautomeric form is colored. The crystalline form of compounds of the present invention comprises predominantly the colorless tautomer.

A first embodiment of the invention is a compound represented by Formula I as described above.

A first embodiment of the invention is a compound whose colorless tautomer is represented by formula I as described above.

Representative compounds according to the invention are those of formula I in which $R_1$, $R_3$, $R_4$, $R_5$, $R_6$, $R_7$, $R_{12}$, $R_{16}$, $R_{18}$ and $R_{19}$ are hydrogen, $X_1$ is carbon, and the other substituents are as shown in Table I:

TABLE I

| Compound | $R_2$ | $R_8$, $R_9$, $R_{10}$, $R_{11}$ | $R_{13}$, $R_{14}$, $R_{15}$ | $R_{17}$ |
|---|---|---|---|---|
| I | $C_6H_5$ | Cl | Me | H |
| II | 4-(O-2-ethyl-1-hexyl)$C_6H_4$ | Cl | H | H |
| III | 3,4-dioctyloxy-$C_6H_3$ | Cl | H | H |
| IV | 4-(2-hydroxy-1-decyloxy)-$C_6H_4$ | Cl | H | H |
| V | 3,4-dioctyloxy-$C_6H_3$ | Cl | H | OMe |
| VI | 2-isopropyl-$C_6H_4$ | F | H | H |
| VII | 2-Methyl-4-decyloxy-$C_6H_3$ | F | H | H |
| VIII | 2-Methyl-4-decyloxy-$C_6H_3$ | F | H | Me |
| IX | 2-Methyl-4-octadecyloxy-$C_6H_3$ | F | H | H |

Preferred compounds according to the invention are III, VII and VIII.

Definitions

The term "alkyl" as used herein refers to saturated straight-chain, branched-chain or cyclic hydrocarbon radicals. Examples of alkyl radicals include, but are not limited to, methyl, ethyl, propyl, isopropyl, n-butyl, tert-butyl, neopentyl, n-hexyl, cyclohexyl, n-octyl, n-decyl, n-dodecyl and n-hexadecyl radicals.

The term "alkenyl" as used herein refers to unsaturated straight-chain, branched-chain or cyclic hydrocarbon radicals. Examples of alkenyl radicals include, but are not limited to, allyl, butenyl, hexenyl and cyclohexenyl radicals.

The term "alkynyl" as used herein refers to unsaturated hydrocarbon radicals having at least one carbon-carbon triple bond. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

The terms "halo" and "halogen," as used herein, refer to an atom selected from fluorine, chlorine, bromine and iodine.

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "carbonyl" as used herein refers to a carbonyl group, attached to the parent molecular moiety through the carbon atom, this carbon atom also bearing a hydrogen atom, or in the case of a "substituted carbonyl" a substituent as described in the definition of "substituted" below.

The term "acyl" as used herein refers to groups containing a carbonyl moiety. Examples of acyl radicals include, but are not limited to, formyl, acetyl, propionyl, benzoyl and naphthyl.

The term "alkoxy", as used herein, refers to a substituted or unsubstituted alkyl, alkenyl or heterocycloalkyl group, as previously defined, attached to the parent molecular moiety through an oxygen atom. Examples of alkoxy radicals include, but are not limited to, methoxy, ethoxy, propoxy, isopropoxy, n-butoxy, tert-butoxy, neopentoxy and n-hexoxy.

The term "aryloxy" as used herein refers to a substituted or unsubstituted aryl or heteroaryl group, as previously defined, attached to the parent molecular moiety through an oxygen atom. Examples of aryloxy include, but are not limited to, phenoxy, p-methylphenoxy, naphthoxy and the like.

The term "alkylamino", as used herein, refers to a substituted or unsubstituted alkyl, alkenyl or heterocycloalkyl group, as previously defined, attached to the parent molecular moiety through a nitrogen atom. Examples of alkylamino radicals include, but are not limited to, methylamino, ethylamino, hexylaminoand dodecylamino.

The term "arylamino", as used herein, refers to a substituted or unsubstituted aryl or heteroaryl group, as previously defined, attached to the parent molecular moiety through a nitrogen atom.

The term "substituted" as used herein in phrases such as "substituted alkyl", "substituted alkenyl", "substituted aryl", "substituted heteroaryl", "substituted heterocycloalkyl", "substituted carbonyl", "substituted alkoxy", "substituted acyl", "substituted amino", "substituted aryloxy", and the like, refers to independent replacement of one or more of the hydrogen atoms on the substituted moiety with substituents independently selected from, but not limited to, alkyl, alkenyl, heterocycloalkyl, alkoxy, aryloxy, hydroxy, amino, alkylamino, arylamino, cyano, halo, mercapto, nitro, carbonyl, acyl, aryl and heteroaryl groups.

According to the invention, there have been provided molecules exhibiting tautomerism in which at least one tautomeric form is colorless, and at least another tautomeric form is colored. Crystallization of the equilibrating mixture of the two tautomeric forms is carried out so as to produce colorless crystals. The solvent chosen to perform the crystallization will typically be one of such polarity (and other chemical properties, such as hydrogen-bonding ability) that the pure colorless crystal form is favored, either in the equilibrium between the colorless and colored forms in solution, or in having lower solubility in the solvent than the colored form. The choice of solvent is usually determined empirically for a particular mixture of tautomers.

Upon conversion of the pure crystalline colorless form, the equilibrium between the two tautomers is re-established in the resulting amorphous (liquid) phase. The proportion of the amorphous material that is colored (i.e., the proportion that is in the colored tautomeric form) may vary, but is preferably at least about 10%.

The colored and colorless tautomeric forms of the molecules of the present invention must meet certain criteria for image quality and permanence. The colorless form, which is preferably the crystalline form, should have minimal visible absorption. It should be stable to light, heating below the melting point, humidity, and other environmental factors such as ozone, oxygen, nitrogen oxides, fingerprint oils, etc. These environmental factors are well known to those skilled in the imaging art. The colored, amorphous form should be stable also to the above mentioned conditions, and in addition should not recrystallize to the colorless form under normal handling conditions of the image. The colored form should have a spectral absorption appropriate for digital color rendition. Typically, the colored form should be yellow (blue-absorbing), magenta (green-absorbing), cyan (red absorbing), or black, without undue absorption in an unintended spectral region. For nonphotographic applications, however, it may be required that the colored form not be one of the subtractive primary colors, but rather a particular spot color (for example, orange, blue, etc.).

The compounds of the invention may be prepared by synthetic processes which are known to those skilled in the art, particularly in view of the state of the art and the specific preparatory examples provided below herein.

Symmetrical rhodamine dyes can be prepared in one step from 3',6'-dichlorofluorans by reacting two equivalents of an aromatic or aliphatic amine as described in U.S. Pat. No. 4,602,263, British Patent No. GB2311075 and German Patent No. DE81056. The novel unsymmetrical rhodamine dyes in this application require a more controlled synthetic pathway in which one equivalent of an indoline is reacted selectively with the 3',6'-dichlorofluoran using aluminum chloride as a catalyst to produce 3'-chloro-6'-indolinofluorans. These products are isolated and purified prior to reacting with a second equivalent of an aromatic or aliphatic amine. Zinc chloride is used as the catalyst for the second addition. German Patent No. DE139727 describes the selective addition of anilines to 3',6'-dichlorofluorans to produce 3'-chloro-6'-arylaminofluorans using a mixture of zinc chloride and zinc oxide at 160° C.

To optimize the chromophore, melting point, degree of coloration, light stability and solubility of the dyes in this application a variety of indolines, anilines and dichlorofluorans are utilized.

5-methoxyindoline and 5-methylindoline are prepared from the corresponding indoles by reduction with sodium cyanoborohydride in acetic acid. 2,3,3-trimethylindoline is prepared from 2,3,3-trimethylindolenine by hydrogenation.

The aromatic amines used in this application are synthesized from 4-nitro-3-methylphenol, 4-nitrophenol and 4-nitrocatechol. The anions of the phenols are generated in dimethylformamide with potassium carbonate and alkylated with a variety of alkylating agents such as 1-bromodecane, 1-bromooctadecane, 1-bromo-2-ethylhexane. Alternatively, the sodium salts of the phenols are alkylated with 1,2-epoxyalkanes using tetrabutylammonium sulfate in a boiling mixture of toluene and water. The resulting 4-nitrophenylethers are reduced to the corresponding anilines using standard methods such as hydrogenation, iron powder, hydrazine or ammonium formate.

The 3',6'-dichlorofluorans are synthesized from the corresponding fluoresceins using thionyl chloride and dimethylformamide in a variation of the method of Hurd described in the Journal of the Amer. Chemical Soc. 59, 112 (1937). 4,5,6,7-tetrafluorofluorescein is prepared according to the procedure of Haugland described in the Journal of Organic Chemistry, 62, 6469 (1997).

The thermal imaging members of the invention can be direct thermal imaging members wherein an image is formed in the member itself or they can be thermal transfer imaging members whereby image-forming material is transferred to an image-receiving member. The melting point of the molecules used in direct thermal imaging members of the present invention is preferably in the range of about 60° C. to about 300° C. Melting points lower than about 60° C. lead to direct thermal imaging members that are unstable to temperatures occasionally encountered during handling of the members before or after imaging, while melting temperatures above about 300° C. render the compounds difficult to colorize with a conventional thermal print head. It should be noted, however, that there are uses for certain novel compounds of the present invention that do not require the use of thermal print heads (for example, laser imaging).

The colors formed by preferred compounds of the present invention are typically cyan, which is to say that the maximum absorption of the preferred compounds in the amorphous state lies between about 600 and about 700 nm. It has been found that the wavelength of maximum absorption of the colored form of compounds of the present invention is longer when substituents $R_8$, $R_9$, $R_{10}$ and $R_{11}$ of formula I are electron-withdrawing relative to hydrogen. Dyes with relatively short maximum absorption wavelengths may appear blue, rather than cyan, and for this reason substituents $R_8$, $R_9$, $R_{10}$ and $R_{11}$ of formula I are preferred to be highly electron-withdrawing, and preferably halogen, when $X_1$ of formula I is a carbon atom and the color cyan is desired.

To form a direct thermal imaging system, the crystalline, colorless form of the compounds of the invention is made into a dispersion in a solvent in which the compound is insoluble or only sparingly soluble, by any of the methods known in the art for forming dispersions. Such methods include grinding, attriting, etc. The particular solvent chosen will depend upon the particular crystalline material. Solvents that may be used include water, organic solvents such as hydrocarbons, esters, alcohols, ketones, nitriles, and organic halide solvents such as chlorinated and fluorinated hydrocarbons. The dispersed crystalline material may be combined with a binder, which may be polymeric. Suitable binders include water-soluble polymers such as poly(vinyl alcohol), poly(vinylpyrrollidone) and cellulose derivatives, water-dispersed latices such as styrene/butadiene or poly (urethane) derivatives, or alternatively hydrocarbon-soluble polymers such as polyethylene, polypropylene, copolymers of ethylene and norbornene, and polystyrene. This list is not intended to be exhaustive, but is merely intended to indicate the breadth of choice available for the polymeric binder. The binder may be dissolved or dispersed in the solvent.

Following preparation of the dispersion of the compound of the present invention, and optional addition of a polymeric binder, the resultant fluid is coated onto a substrate using any of the techniques well-known in the coating art. These include slot, gravure, Meyer rod, roll, cascade, spray, and curtain coating techniques. The image-forming layer so formed is optionally overcoated with a protective layer or layers.

If materials of the present invention are used to prepare an imaging medium of the type described in copending U.S. patent application Ser. No. 10/151,432 filed May 20, 2002 the process described above is followed for each of the imaging layers. Successive layers may be coated sequentially, in tandem, or in a combination of sequential and tandem coatings.

EXAMPLES

The invention will now be described further in detail with respect to specific embodiments by way of examples, it being understood that these are intended to be illustrative only and the invention is not limited to the materials, amounts, procedures and process parameters, etc. recited therein. All parts and percentages recited are by weight unless otherwise specified.

Example 1

Synthesis of Intermediates.

Step 1A. Alkylation of 4-nitrocatechol

4-Nitrocatechol (23.26 g, 0.15 mol) and potassium carbonate (124.38 g, 0.9 mol) were placed in a one liter 3-neck flask fitted with a mechanical stirrer. Anhydrous dimethylformamide (350 mL) was added to this mixture followed by the addition to the suspension, dropwise, of 1-bromo octane (63.73 g, 0.33 mol). The reaction mixture was heated at 110° C. for 24 hours. The reaction was followed by TLC (2% methanol in methylene chloride). After the completion of the reaction the contents were cooled and poured dropwise with stirring into ice-water (1 L). The mixture was stirred for one hour and filtered. The collected solid was washed thoroughly with water, air-dried and then dried in vacuo at 30° C. This process produced brown crystals: (54.8 g, 0.144 mol, 96% yield). These crystals were used without further purification.

Step 1B. Synthesis of 3,4-dioctyloxyaniline 3,4-Dioctyloxynitrobenzene (25.25 g, 0.067 mol) was dissolved in ethyl acetate (250 mL) in a Parr bottle. 10% Pd on charcoal (3.5 g) was added and the mixture was hydrogenated (5–6 hr) at 50 psi until the hydrogen uptake ceased. The reaction mixture was filtered and evaporated. The aniline was obtained as a dark syrup. (22.5 g, 0.064 mol, 97% yield).

The structure was corroborated by NMR and mass spectroscopy.

Step 1C. Synthesis of 2-methyl-4-decyloxynitro benzene

To a solution of 3-methyl-4-nitrophenol (45 g, 0.294 mol) in dimethylformamide (270 mL) there were added 1-bromodecane (65 g, 0.294 mol) and potassium carbonate (121.8 g, 0.882 mol). The reaction mixture was heated to 115° C. and stirred at that temperature for 48 hours. The reaction mixture was cooled and poured into water (4 L), stirred for 0.5 hour and extracted with two portions of ethyl acetate (1.5 L and 600 mL). The combined organic extracts were washed with 5% aqueous solution sodium bicarbonate (1 L), water (1 L and 0.5 L), dried over sodium sulfate and concentrated to give the crude product (90 g, 0.294 mol, 100% yield). This product was used in the next step without purification.

Step 1D. Synthesis of 2-methyl-4-decyloxyaniline

The mixture of crude 2-methyl-4-decyloxynitrobenzene (90 g, 0.294 mol), methanol (246 mL), concentrated hydrochloric acid (159 mL) and dioxane (70 mL) was heated to 75° C. Iron powder (49.9 g, 0.89 mol) was added in small portions with vigorous stirring. After the addition was complete the reaction mixture was stirred at 75° C. for another 20 minutes and poured warm into water (3 L), stirred for 30 minutes and the pH adjusted to 11.0 by addition of aqueous potassium carbonate solution. Dichloromethane (3 L) was added and the mixture was stirred intensively for 1 hour. The layers were separated and the organic layer dried over sodium sulfate and passed through a thin pad of silica gel. The solvent was evaporated to dryness to give a brown oil (58.5 g, 0.22 mol, 76% yield).

Step 1E. Synthesis of 2-methyl-4-octadecyloxynitrobenzene:

1-Bromooctadecane (43.54 g, 0.131 mol) and potassium carbonate (54.15 g, 0.392 mol) were added to a solution of 3-methyl-4-nitrophenol (20 g, 0.131 mol) in dimethylformamide (120 mL) The reaction mixture was heated to 110° C. and stirred at this temperature for 60 hours. The reaction mixture was cooled and poured into water (2 L), stirred for 0.5 hour and extracted with methylene chloride (1 L). The organic extract was washed with 5% aqueous solution sodium bicarbonate (0.5 L), water (2×0.6 L), dried over sodium sulfate and concentrated to give (60 g) of crude product. This product was used in the next step without purification.

Step 1F. Synthesis of 2-methyl-4-octadecyloxyaniline

The mixture of crude 2-methyl-4-octadecyloxynitrobenzene (30 g, ca. 0.065 mol), methanol (55 mL), concentrated hydrochloric acid (40.5 mL) and dioxane (50 mL) was heated to 85° C. Iron powder (11.2 g, 0.20 mol) was added in small portions with intensive stirring. After the addition was complete the reaction mixture was stirred at 85° C. for another 3 hours and poured warm into water (800 mL), stirred for 30 minutes and the pH adjusted to 10.0 by addition of aqueous potassium carbonate solution. Dichloromethane (1.0 L) was added and mixture was stirred intensively for 1 hour. The layers were separated and the organic layer was washed with water (2×500 mL) and dried over sodium sulfate. The solvent was evaporated to give an oil (20 g, 0.053 mol, 82% yield), which solidified on standing.

The structure of this material was corroborated by proton NMR and mass spectroscopy.

Step 1G. Synthesis of 2-ethyl-1-hexyloxynitro benzene

4-Nitrophenol (10 g, 72mmol) and potassium carbonate (30.4 g, 0.22 mol) were added to dimethylformamide (80 mL) at room temperature and the mixture was stirred with heating at 100° C. for 2 hours. 2-Ethyl-1-hexyl bromide (16.7 g, 86mmol) was slowly added to the mixture for 20 minutes. After the addition the mixture was further stirred at 150° C. for 3 hours. After cooling, the reaction mixture was poured into water (500 mL) and then the mixture was extracted with methylene chloride. After evaporation of solvent, the residual product was isolated as an oil in high yield (18 g, 71.6 mmol, 99% yield).

Step 1H. Synthesis of 2-ethyl-1-hexyloxy aniline

2-Ethyl-1-hexyloxynitro benzene (18 g, 72 mmol) was dissolved in isopropanol (80 mL) and 10% Pd/C (1 g) was slowly added to the mixture in a Parr pressure bottle. The mixture was hydrogenated at 40 psi for 5 hours and the mixture was filtered to remove Pd/C followed by evaporation of the solvent to give the oily product in quantitative yield (15.9 g, 72 mmol, 100% yield).

Step 1I. Synthesis of 4-(2-hydroxy-1-decyloxy)nitrobenzene

The sodium salt of 4-nitrophenol (28.19 g, 0.175 mol) was dissolved in water (50 mL) and toluene (300 mL) and tetrabutylammonium sulfate (6.0 g) was added. 1,2-Epoxydecane (27.3 g, 0.175 mol) was added to this mixture and the reaction was heated at 100° C. for 5 days. The toluene layer was separated and washed with water (4×75 mL), 1N hydrochloric acid (2×75 mL) and water (75 mL). The organic layer was dried over sodium sulfate, filtered and the solvent removed. The crude product was purified by silica gel chromatography (2–3% methanol/methylene chloride) to afford 4-(2-hydroxy-1-decyloxy)nitrobenzene as a pale oil (20 g, 0.68 mol, 39% yield).

Step 1J. Synthesis of 4-(2-hydroxy-1-decyloxy)aniline 4-(2-hydroxy-1-decyloxy)nitrobenzene (20 g, 0.68 mol) was dissolved in ethyl acetate (200 mL) and 10% palladium on carbon (2.5 g) was added to a Parr pressure bottle. The contents were then hydrogenated at 50 psi until hydrogen uptake ceased. The catalyst was removed by suction filtration through a pad of Celite. Removal of solvent afforded 4-(2-hydroxy-1-decyloxy)aniline in quantitative yield (18.0 g, 0.68 mol, 100% yield) as a tan solid.

The structure was confirmed by NMR and mass spectroscopy.

Step 1K. Synthesis of 5-methoxyindoline

5-Methoxyindole (50 g, 0.34 mol) was dissolved in glacial acetic acid (500 mL) in a 3 L 3-necked flask fitted with a mechanical stirrer, a dropping funnel and a thermometer. The solution was cooled to 10–12° C. with an ice bath and sodium cyanoborohydride (64 g, 1.0 mol) was added in portions while ensuring the temperature remained at or below 15–16° C. After the addition was complete the cooling bath was removed and the reaction was warmed to ambient temperature for 0.5 hour. TLC (1:1 EtOAc/hexane) confirmed a complete reaction. The reaction was cooled to 5–10° C. and 50% aqueous sodium hydroxide was added until the pH was 8–10. The product oiled out and was extracted with ethyl acetate (3×700 mL). The combined organic layers were washed with water (2×500 mL) and brine (400 mL), dried over anhydrous potassium carbonate, filtered and concentrated to afford 5-methoxyindoline (50 g, 0.337 mol, 99% yield) as a thick oil. This product was used without further purification.

The structure was corroborated by NMR spectroscopy.

Step 1L. Synthesis of 5-methylindoline:

5-Methylindoline was prepared from 5-methylindole using the procedure described for the preparation of 5-methoxyindoline. 5-Methylindole (11 g, 0.0835 mol) in glacial acetic acid (150 mL) in a 1 L 3-necked flask was reduced at 10–15° C. with sodium cyanoborohydride (15.8 g, 0.251 mol). Extraction with ethyl acetate provided 5-methylindoline (11 g, 0.0832 mol, 99% yield) as a thick oil which was used without further purification.

The structure was corroborated by NMR spectroscopy.

Step 1M. Synthesis of 3',6',4,5,6,7-hexachlorofluoran:

Acetonitrile (680 mL), dimethylformamide (7 mL), tetrachlorofluorescein (170 g, 0.36 mol) and thionyl chloride (215 g, 1.8 mol) were added to a 3-liter 3-neck round bottom flask fitted with a mechanical stirrer, condenser and nitrogen inlet tube. Upon heating, a solution was briefly obtained followed by gradual crystallization of the product. The mixture was further heated at reflux (72° C.) for six hours. After cooling to room temperature, water (100 mL) was slowly and carefully added. The product was filtered and washed well with acetonitrile. Air drying provided a pale violet solid (141.5 g, 0.279 mol, 77% yield). The crude product was stirred in dimethylformamide (425 mL), heated to 100° C., and allowed to stand overnight. The pale violet crystals were filtered, washed with dimethylformamide followed by methanol and dried under vacuum at 60° C. to provide hexachlorofluoran (98.7 g, 0.195 mol, 54% yield).

Assay by HPLC was 97% by area.

Step 1N. Synthesis of 3'-indolino-6',4,5,6,7-pentachlorofluoran:

Hexachlorofluoran (5.07 g, 10 mmol), 2,6-lutidine (1.07 g, 10 mmol), aluminum chloride (9.33 g, 70 mmol) and sulfolane (50 mL) were added to a 100 mL 3-neck round bottom flask fitted with a mechanical stirrer, condenser, thermometer and nitrogen inlet tube. The mixture was heated to 100° C. and indoline (1.19 g, 10 mmol) was added. The temperature was raised to 180° C. and heating continued for 6 hours. After cooling to room temperature, the mixture was poured into cold water (250 mL) with rapid agitation. The blue-gray solid was filtered, washed with water and air-dried providing the crude product (5 g). The crude product was stirred in dimethylformamide (20 mL), heated to 100° C. and allowed to stand overnight. The resulting pale green solid was filtered, washed first with dimethylformamide followed by methanol and dried under vacuum at 60° C. to provide 3-indolinopentachlorofluoran (3.60 g, 6.1 mmol, 61% yield). Assay by HPLC was 97% by area.

Step 1P. Synthesis OF 3'-(5-methoxyindolino)-6',4,5,6,7-pentachlorofluoran

Hexachlorofluoran (20 g, 0.0394 mol), aluminum chloride (20.8 g, 0.156 mol) and sulfolane (100 g) were added to a 250 mL 3-neck round bottom flask fitted with a mechanical stirrer, condenser, thermometer and nitrogen inlet tube. The mixture was heated to 120° C. and 5-methoxyindoline (12 g, 0.081 mol) was added. The reaction mixture was heated overnight at 120° C. After cooling to room temperature, the mixture was poured into cold water (1 L) with rapid agitation. The solid was filtered, washed with water and air-dried for several days followed by vacuum drying at 70° C. to give the crude product (25.5 g, 0.041 mol, 104% yield) which was used without further purification.

Step 1Q. Synthesis of 4,5,6,7-tetrafluorofluorescein

Using a mechanical stirrer, tetrafluorophthalic anhydride (50 g, 0.227 mol) was dissolved in methanesulfonic acid (221 mL). The anhydride dissolved completely as the temperature reached 40° C. When the temperature had reached 120° C., resorcinol (62.3 g, 0.568 mol) was added in 3 portions giving enough time between additions for the material to go into solution. The solution turned pale red. An HPLC of the reaction mixture was taken at the start of the reaction and every hour thereafter. The reaction was complete after three hours. Heating was stopped and the reaction mixture was allowed to cool to ambient temperature. The dark semi-solid residue was slowly poured into rapidly stirred ice water (2 L). A fine, olive-green solid precipitated in the water. The solid suspension was extracted with ethyl acetate (1 L) followed by further extractions with ethyl acetate (4×400 mL). The organic fractions were combined and dried over anhydrous magnesium sulfate (250 g). After stirring overnight, the drying agent was removed by vacuum filtration through a Celite pad. The ethyl acetate was removed on a rotary evaporator to give a dark brown-black solid (95 g) that was not further purified. The solid was dried in a vacuum desiccator overnight at 70° C.

Step 1R. Synthesis of 3',6'-Dichloro-4,5,6,7-tetrafluoran

Using a mechanical stirrer, tetrafluorofluorescein (95 g, ca. 0.235 mol) was suspended in a mixture of acetonitrile (350 mL) and dimethylformamide (5.8 mL). Thionyl chloride (79 mL, 129.3 g, 1.08 mol) was added to this mixture. The reaction mixture was heated to reflux for 4 hours. HPLC showed complete conversion after 4 hours. The excess acetonitrile and excess thionyl chloride were removed by distillation in a stream of nitrogen. When nearly all of the solvent had been removed, the solid was resuspended in a solution of acetonitrile/water (95:5). The violet-brown solid was collected by vacuum filtration, washed with 95:5 acetonitrile/water (500 mL) followed by drying in a vacuum desiccator at 70° C. for 4 hours to give the desired product (84 g, 0.19 mol, 80% yield).

Step 1S. Synthesis of 3'-indolino-6'chloro-4,5,6,7-tetrafluorofluoran

3',6'-Dichloro-4,5,6,7-tetrafluorofloran (20 g, 0.045 mol), 2,6-lutidine (4.74 g, 0.045 mol) and sulfolane (56 mL) were added to a 250 mL 3-neck round bottom flask fitted with a mechanical stirrer. Aluminum chloride (40.2 g, 0.28 mol) was added in small portions and the resulting mixture was stirred for 20 minutes. The temperature rose to 110° C. Indoline (5.13 g, 0.045 mol) was added slowly followed by 2,6-lutidine (4.74 g, 0.045 mol) and the reaction was heated at 110° C. for 5 hours. The reaction was followed to completion by HPLC. The reaction was poured into a mixture of crushed ice and water with vigorous agitation. The dark blue solid was collected by suction filtration, washed with water and dried under vacuum. The crude product was passed through a silica gel plug (300 g) using methylene chloride to elute. Removal of solvent provided the indolinofluoran as a yellow-green foam (16 g, 0.031 mol, 68% yield).

The structure was confirmed by NMR and mass spectroscopy.

Step 1T. Synthesis of 3'-(5-methylindolino)-6'chloro-4,5,6,7-tetrafluorofluoran

3',6'-Dichloro-4,5,6,7-tetrafluorofluoran (13.23 g, 0.030 mol), 2,6-lutidine (6.43 g, 0.060 mol) and sulfolane (30 Ml) were added to a 100 mL 3-neck round bottom flask fitted with a condenser. Aluminum chloride (16 g, 0.120 mol) was added followed by 5-methylindoline (4.0 g, 0.030 mol) and the reaction was heated at 110–120° C. for 20 hours under nitrogen. The reaction mixture was poured into a mixture of crushed ice, water, and hydrochloric acid (500 mL) with vigorous agitation and stirred for 0.5 hour. The solid was dissolved in ethyl acetate and washed with 10% sodium bicarbonate solution. The organic layer was separated, dried over sodium sulfate and concentrated The crude product was passed through a short column of silica gel using methylene chloride to elute. Removal of solvent provided the 3'-(5-methylindolino)-6'-chloro-4,5,6,7-tetraflourofluoran as a solid (4.6 g, 8.5mmol, 28% yield).

The structure was confirmed by NMR and mass spectroscopy.

Example II

Synthesis of Dye I

A mixture of hexachlorofluoran (2.0 g, 3.9 mmol), 2,3,3-trimethylindoline (0.9 g; 5.9 mmol), zinc chloride (1.6 g; 11.8 mmol), and zinc oxide (0.5 g; 5.9 mol) in sulfolane (6 g) was stirred with heating at 190° C. for 4 hours. To this mixture was added aniline (0.8 g; 7.9 mmol) and the mixture was then further stirred with heating at 160° C. for 14 hours. The mixture was cooled to 50° C. and quenched into 2N HCl (100 mL). The crude solid was isolated by filtration, washed with water several times and taken up in methylene chloride (150 mL). The methylene chloride solution was washed with sat. sodium bicarbonate (2×100 mL), dried over magnesium sulfate and the solvent removed. The residual solid was purified by column chromatography on silica gel (eluted with 30% ethyl acetate in hexane) to give 0.6 g pure product (22% yield) and then recrystallized from ca. 10% acetone in hexane to give colorless crystalline product, m.p. 210–215° C. (0.35 g, 13% yield).

The structure was confirmed by proton NMR and mass spectroscopy.

Example III

Synthesis of Dye II

A mixture of hexachlorofluoran (2.0 g, 3.9 mmol), indoline (0.7 g, 5.9 mmol), zinc chloride (1.6 g, 11.8 mmol), and zinc oxide (0.5 g, 5.9 mmol) in sulfolane (6 g) was stirred with heating at 145° C. for 90 minutes. To this mixture was added 4-(2-ethyl-1-hexyloxy) aniline (2.7 g, 7.9 mmol) and the mixture was further stirred with heating at 160° C. for 5 hours. The mixture was cooled to 50° C. and quenched into 2N HCl (100 mL). The crude solid was isolated by filtration, washed with water several times and taken up in methylene chloride (150 mL). The methylene chloride solution was washed with sat. sodium bicarbonate (2×100 mL), dried over magnesium sulfate and the solvent was evaporated. The residual solid was purified by column chromatography (10% ethyl acetate in methylene chloride) to give 1.2 g pure product (39% yield) and recrystallized from approximately 10% acetone/hexane to give colorless crystalline product (0.55 g, m.p. 180–182° C., 18% yield).

The structure was confirmed by proton NMR and mass spectroscopy.

Example IV

Synthesis of Dye III

Pentachloroindolinofluoran (11.8 g, 20 mmol), $ZnCl_2$ (8.2 g, 60 mmol) and ZnO (2.43 g, 30 mmol) were added to a 250 ml round bottom flask containing sulfolane (30 g) and the flask warmed to dissolve the solids. To the hot blue solution was added 3,4-dioctyloxyaniline (13.96 g, 40 mmol) and the flask was placed with an air condenser into an oil bath preheated to 140° C. The reaction mixture was stirred at that temperature for 2 hours. The reaction was followed by TLC (25% ethyl acetate in hexane) until complete. The reaction mixture was cooled and 2N HCl (400 mL) was added followed by trituration with a spatula to break the large blue mass to a crystalline powder. The reaction mixture was filtered and washed copiously with water. The crude product was dissolved in ethyl acetate (1200 mL) and extracted with 10% $Na_2CO_3$ (2×250 mL), followed by water and brine (250 mL each). The organic layer was dried over sodium sulfate and evaporated to yield crude blue product (23 g).

The crude product was purified on a silica gel column (1.5 Kg) packed in methylene chloride. The product was eluted with 10% ethyl acetate/methylene chloride (5 L). Pure fractions were pooled to obtain the product as a glass (13.5 g) which was crystallized from 10% acetone in hexane to obtain a first crop of colorless crystals (8.5 g, 9.4 mmol, 47% yield). Recrystallization of the mother liquor provided a second crop of crystals (2.5 g, 2.7 mmol, 13.5% yield). The overall yield was 11.0 g, 12.1 mmol, 60.5% yield.

NMR analysis and mass spectroscopy confirmed the structure.

Example V

Synthesis of Dye IV

3'-Indolinopentachlorofluorescin (2.15 g, 3.6 mmol), 4-(2-hydroxy-1-decyloxy)aniline (1.81 g, 6.8 mmol), zinc chloride (1.5 g, 11 mmol), zinc oxide (0.45 g, 5.6 mmol) and tetramethylene sulfone (8 g) were added to a 100-mL flask. The reaction mixture was heated at 150° C. for 12 hours under an atmosphere of nitrogen. The cooled mixture was poured into 2N hydrochloric acid (100 mL). A dark blue precipitate was obtained and filtered and washed with 0.5N aq. hydrochloric acid solution (100 mL) and water (100 mL). The crude product was purified by silica gel column chromatography (loaded and eluted with 500 ml of methylene chloride, followed by 500 ml of 1% methanol/methylene chloride). The solvent was removed by rotary evaporation to collect a dark blue powder (2.3 g, 2.77 mmol, 77% yield). Pale greenish crystals were obtained by recrystallization from 10% acetone/hexanes. m.p: 156–158° C.

The structure was confirmed by proton NMR and mass spectroscopy.

Example VI

Synthesis of Dye V

A mixture of hexachlorofluoran (1.0 g, 1.9 mmol), 5-methoxyindoline (0.5 g, 3.0 mmol), zinc chloride (0.8 g, 5.9 mmol), and zinc oxide (0.3 g, 2.5 mmol) in sulfolane (4 g) was stirred with heating at 145° C. for 2 hours. To this mixture was added 3,4-dioctyloxyaniline (1.4 g, 4.0 mmol) and the mixture was further stirred with heating at 160° C. for 5 hours. The mixture was cooled to 50° C. and quenched into 2N HCl (100 mL). The crude solid was isolated by filtration, washed with water several times and taken up in methylene chloride (150 mL). The methylene chloride solution was washed with sat. sodium bicarbonate (2×100 mL), dried over magnesium sulfate and the solvent was removed. The residual solid was purified by column chromatography on silica gel eluted with 20% ethyl acetate in methylene chloride to give pure product (0.80 g, 0.836 mmol, 44% yield) which was recrystallized from acetonitrile to give colorless crystalline product (0.35 g, 0.836 mmol, 19% yield) m.p. 117–119° C.

The structure was confirmed by proton NMR and mass spectroscopy.

Example VII

Synthesis of Dye VI

A mixture of 3'-indolino-6'-chloro-4,5,6,7-tetrafluorofloran (1.0 g, 1.9 mmol), zinc chloride (0.8 g, 5.7 mmol), zinc oxide (0.2 g, 2.8 mmol), and 2-isopropylanilne (0.5 g, 3.8 mmol) in sulfolane (4 g) was stirred with heating at 160° C. for 14 hours. The mixture was cooled to 50° C. and quenched into 2N HCl (100 mL). The crude solid was isolated by filtration, washed with water several times and taken up in methylene chloride (150 mL). This methylene chloride solution was washed with sat. sodium bicarbonate (2×100 mL), and dried over magnesium sulfate to remove the solvent he residual solid was purified by column chromatography on silica gel eluted with 35% ethyl acetate in methylene chloride to give pure product (0.60 g, 0.95 mmol, 50% yield) which was recrystallized from 10% acetone in hexane to give colorless crystalline product (0.3 g, 0.475 mmol, 25% yield) m.p. 209–210° C.

The structure was confirmed by proton NMR and mass spectroscopy.

Example VIII

Synthesis of Dye VII

A mixture of 3'-indolino-6'-chloro-4,5,6,7-tetrafluorofluoran (7.80 g, 15 mmol), zinc chloride (6.13 g, 45 mmol), zinc oxide (1.22 g, 15 mmol), and 2-methyl-4-decyloxyaniline (7.89 g, 30 mmol) in sulfolane (30 g) was stirred with heating at 160–170° C. for 24 hours. Analysis by TLC (30% ethyl acetate/methylene chloride) showed a major product at Rf=0.5 with a mass spectrum consistent with the product (M+1=751). The reaction mixture was poured onto a mixture of ice/water/hydrochloric acid, stirred for ½ hour, filtered and dried. The crude product was dissolved in ethyl acetate (700 mL) and stirred for one hour with 10% sodium bicarbonate solution (300 mL). After filtration through a pad of Celite the organic layer was separated, dried over sodium sulfate and concentrated to a thick oil. Column chromatography on silica gel (400 g, 10–30% ethyl acetate/methylene chloride) provided pure fractions which were concentrated and recrystallized from acetone/hexane to yield colorless crystals (5.85 g), m.p. 137–139° C. A second crop (1.0 g) was obtained to give a total of 6.85 g (9.12 mmol, 61% yield).

The structure was confirmed by NMR and mass spectroscopy.

Example IX

Synthesis of Dye VIII

A mixture of 3'-(5-methylindolino)-6'-chloro-4,5,6,7-tetrafluorofluoran (1.343 g, 2.5 mmol), zinc chloride (1.022 g, 7.5 mmol), zinc oxide (0.203 g, 2.5 mmol), and 2-methyl-4-decyloxyaniline (1.375 g, 5 mmol) in sulfolane (5 g) was stirred with heating at 160–175° C. for 24 hours. The reaction mixture was poured onto a mixture of ice/water/hydrochloric acid, stirred for ½ hour, filtered and dried. The crude product was dissolved in methylene chloride, treated with triethylamine (7 mL) and evaporated. Column chromatography on silica gel (250 mL, 50% ethyl acetate/methylene chloride) provided pure fractions which were concentrated and recrystallized from acetone/hexane to yield colorless crystals (0.700 g, 0.915 mmol, 37% yield) m.p. 170–171.5° C.

The structure was confirmed by NMR and mass spectroscopy.

Example X

Synthesis of Dye IX

A mixture of 3'-indolino-6'-chloro-4,5,6,7-tetrafluorofluoran (1.0g, 1.9mmol), zinc chloride (0.8 g, 5.7 mmol), zinc oxide (0.2 g, 2.8 mmol), and 2-methyl-4-octadecyloxyanilne (1.4 g, 3.8 mmol) in sulfolane (4 g) was stirred with heating at 160° C. for 14 hours. The mixture was cooled to 50° C. and quenched into 2N HCl (100 mL). The crude solid was isolated by filtration, washed with water several times and taken up in methylene chloride (150 mL). This methylene chloride solution was washed with sat. sodium bicarbonate (2×100 mL) and dried over magnesium sulfate to remove the the solvent. The residual solid was purified by column chromatography on silica gel eluted with 35% ethyl acetate in methylene chloride to give pure product (1.0 g, 116 mmol, 61% yield) which was recrystallized from 10% acetone in hexane to give colorless crystalline product (0.5 g, 0.57 mmol, 30% yield); m.p. 136–138° C.).

The structure was confirmed by NMR and mass spectroscopy.

Although the invention has been described in detail with respect to various preferred embodiments, it is not intended to be limited thereto, but rather those skilled in the art will recognize that variations and modifications are possible which are within the spirit of the invention and the scope of the appended claims.

What is claimed is:

1. A process for the preparation of a compound represented by the formula (1)

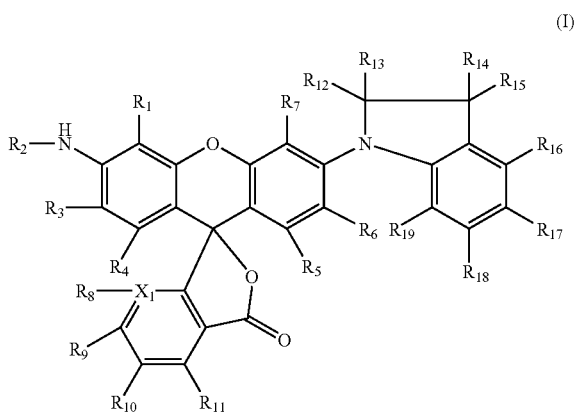

(I)

wherein:
- $R_1$, $R_3$, $R_4$, $R_5$, $R_6$ and $R_7$ are each independently selected from the group consisting of hydrogen, alkyl, substituted alkyl, alkenyl, substituted alkenyl, alkynyl, substituted, alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;
- $R_2$ is selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, sulfonyl, aryl, substituted aryl, heteroaryl, substituted heteroaryl, substituted oxygen, substituted nitrogen and substituted sulfur;
- $R_8$ is absent or selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;
- $R_9$, $R_{10}$ and $R_{11}$ are independently selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;
- $R_{12}$, $R_{13}$, $R_{14}$ and $R_{15}$ are independently selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, aryl, substituted aryl, heteroaryl, and substituted heteroaryl;
- $R_{16}$, $R_{17}$, $R_{18}$ and $R_{19}$ are independently selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur; and
- $X_1$ is carbon or nitrogen, comprising the steps of:
  (a) preparing a substituted or unsubstituted 3'-chloro-6'-indolinofluoran by combining a substituted or unsubstituted indoline with a substituted or unsubstituted 3',6-dichlorofluoran;
  (b) isolating said substituted or unsubstituted 3'-chloro-6'-indolinofluoran; and
  (c) combining said substituted or unsubstituted 3'-chloro-6'-indolinofluoran with a substituted or unsubstituted aniline;
  wherein said steps (a), (b) and (c) are carried out in the order recited.

2. The process of claim 1 wherein the reaction mixture used in the preparation of said substituted or unsubstituted 3'-chloro-6' indolinofluoran comprises aluminum chloride or zinc chloride.

3. The process of claim 1 wherein the solvent used in the preparation of said substituted or unsubstituted 3'-chloro-6'-indolinofluoran comprises sulfolane.

4. The process of claim 1 wherein the reaction mixture used in the preparation of said substituted or unsubstituted 3'-chloro-6'-indolinofluoran comprises 2,6-lutidine.

5. The process of claim 1 further comprising the step of:
  (b') purifying said substituted or unsubstituted 3'-chloro-6'-indolinofluoran;
  wherein said step (b') immediately follows said step (b).

6. The process of claim 1 further comprising the step of:
  (d) purifying said compound represented by formula (1) by recrystallization;
  wherein said step (d) is carried out after step (c).

7. The process of claim 6 wherein the solvent used in said recrystallization is a mixture of acetone and hexane.

\* \* \* \* \*